US012551430B2

(12) United States Patent
Magee et al.

(10) Patent No.: US 12,551,430 B2
(45) Date of Patent: Feb. 17, 2026

(54) SULFATE-FREE CLEANSING COMPOSITIONS COMPRISING PEG/PPG-DIMETHICONES

(71) Applicant: L'OREAL

(72) Inventors: Rachel N. Magee, Westfield, NJ (US); Kazumitsu Kawakami, Westfield, NJ (US); Liliana Xavier, Mountainside, NJ (US)

(73) Assignee: L'OREAL, Paris (FR)

( * ) Notice: Subject to any disclaimer, the term of this patent is extended or adjusted under 35 U.S.C. 154(b) by 307 days.

(21) Appl. No.: 18/343,254

(22) Filed: Jun. 28, 2023

(65) Prior Publication Data

US 2025/0000779 A1 Jan. 2, 2025

(51) Int. Cl.

| | |
|---|---|
| ***C11D 1/94*** | (2006.01) |
| ***A61K 8/34*** | (2006.01) |
| ***A61K 8/37*** | (2006.01) |
| ***A61K 8/39*** | (2006.01) |
| ***A61K 8/44*** | (2006.01) |
| ***A61K 8/46*** | (2006.01) |
| ***A61K 8/73*** | (2006.01) |
| ***A61K 8/81*** | (2006.01) |
| ***A61K 8/894*** | (2006.01) |
| ***A61Q 5/02*** | (2006.01) |
| ***A61Q 5/12*** | (2006.01) |

(52) U.S. Cl.

CPC .............. *A61K 8/894* (2013.01); *A61K 8/345* (2013.01); *A61K 8/375* (2013.01); *A61K 8/39* (2013.01); *A61K 8/442* (2013.01); *A61K 8/466* (2013.01); *A61K 8/737* (2013.01); *A61K 8/817* (2013.01); *A61Q 5/02* (2013.01); *A61Q 5/12* (2013.01); *A61K 2800/596* (2013.01)

(58) Field of Classification Search

CPC .. C11D 1/12; C11D 1/143; C11D 1/37; C11D 1/66; C11D 1/83; C11D 1/88; C11D 1/90; C11D 3/0094; C11D 3/2041; C11D 3/3738; C11D 3/43

See application file for complete search history.

(56) References Cited

U.S. PATENT DOCUMENTS

| | | | | |
|---|---|---|---|---|
| 7,670,615 | B2 | 3/2010 | Veeger et al. | |
| 8,124,115 | B2 | 2/2012 | Veeger et al. | |
| 8,865,145 | B2 | 10/2014 | Molenda et al. | |
| 2008/0085849 | A1* | 4/2008 | Cannell .................. | C11D 3/384 510/129 |
| 2009/0178210 | A1* | 7/2009 | Bistram ................... | A61K 8/39 8/431 |
| 2013/0259821 | A1 | 10/2013 | Henning et al. | |
| 2014/0119655 | A1 | 5/2014 | Liu et al. | |
| 2018/0280270 | A1 | 10/2018 | Rughani et al. | |
| 2021/0196606 | A1* | 7/2021 | Shi ......................... | A61Q 5/065 |
| 2023/0037788 | A1* | 2/2023 | Shi ......................... | A61K 8/365 |
| 2024/0065956 | A1* | 2/2024 | Wadhwani ............... | A61Q 5/10 |
| 2024/0216260 | A1* | 7/2024 | Kawakami ............. | A61K 8/416 |

FOREIGN PATENT DOCUMENTS

| | | | |
|---|---|---|---|
| EP | 2113244 | A1 | 11/2009 |
| JP | 2021024856 | A | 2/2021 |

OTHER PUBLICATIONS

Preliminary Search Report and Written Opinion issued on Apr. 12, 2024 for corresponding French Application No. FR 2309244.

"Christophe Robin Colour Shield Shampoo", https://www.adorebeauty.com.au/p/christophe-robin/christophe-robin-colour-shield-shampoo.html.

"Keratin Care Smoothing Shampoo", https://www.ulta.com/p/keratin-care-smoothing-shampoo-xlsImpprod10111262.

"Ingredients for Keratin Perfect Keratin Daily Smoothing Shampoo," https://www.cvs.com/shop/ingredients/keratin-perfect-keratin-daily-smoothing-shampoo-12-oz-prodid-277737.

"Senscience Smooth Shampoo," https://sleekshop.com/products/senscience-smooth-shampoo.html?sku=27402-10-2-oz&utm_medium=product_shelf.

"Shampoo 300ml Silk Moisture Senscience," https://www.easypara.co.uk/shampoo-300ml-silk-moisture-senscience.html.

* cited by examiner

*Primary Examiner* — Charles I Boyer
(74) *Attorney, Agent, or Firm* — POLSINELLI PC

(57) ABSTRACT

The present disclosure is drawn to cleansing compositions that are free or essentially free from sulfate-based surfactants. The cleansing compositions include: (a) one or more PEG/PPG dimethicones; (b) propylene glycol; (c) a plurality of surfactants, the plurality of surfactants comprising: (c)(i) one or more non-sulfate anionic surfactants; (c)(ii) one or more amphoteric surfactants; and (c)(iii) one or more nonionic surfactants; (d) one or more cationic conditioning polymers; (e) optionally, one or more water-soluble organic solvents, other than propylene glycol; and (f) water. The cleansing compositions are particularly useful in methods for cleansing hair and providing conditioning benefits to the hair.

17 Claims, No Drawings

SULFATE-FREE CLEANSING COMPOSITIONS COMPRISING PEG/PPG-DIMETHICONES

FIELD OF THE DISCLOSURE

The present disclosure relates to sulfate-free cleansing compositions and methods for cleansing the hair or body with the compositions.

BACKGROUND

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing, solubilizing, and dispersing properties but are usually less irritating than anionic surfactants. Nonionic surfactants, however, often exhibit less foaming ability and do not provide any enhancement to viscosity (e.g., often a composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions should also rinse away from the body with ease. However, the addition of a particular component to a cleansing composition often will enhance one desired property to the detriment of another desired property. It is therefore difficult to achieve a perfect balance of desirable performance properties.

SUMMARY OF THE DISCLOSURE

The present disclosure relates to cleansing compositions that are free from sulfate-based surfactants. Sulfate-based surfactants are common in cleansing compositions, such as shampoo compositions, due to their strong cleansing properties. These properties, however, can be harsh, especially when used to clean delicate hair. Sulfate-based surfactants, like non-sulfate-based surfactants, remove unwanted dirt and contamination, but sulfate-based surfactants tend to remove natural oils from the hair that normally help prevent dryness. Despite lacking sulfate-based surfactants, the cleansing compositions of the instant disclosure have powerful cleansing properties. The inventors discovered that use of one or more PEG/PPG dimethicones and propylene glycol impart improved cosmetic properties to the compositions. For example, the inventors discovered the cleansing compositions preserve the color of artificially colored hair, improve shine, moisturize hair, and impart a pleasant tactile feel to the hair.

The cleansing compositions include:

(a) one or more PEG/PPG dimethicones;
(b) propylene glycol;
(c) a plurality of surfactants, the plurality of surfactants comprising:
  (c)(i) one or more non-sulfate based anionic surfactants;
  (c)(ii) one or more amphoteric surfactants; and
  (c)(iii) one or more nonionic surfactants;
(d) one or more cationic conditioning polymers;
(e) optionally, one or more water-soluble solvents other than propylene glycol; and
(f) water.

Nonlimiting examples of PEG/PPG-dimethicones include PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 Dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone, PEG/PPG-27/27, bis-PEG/PPG 18/6 dimethicone, PEG/PPG 30/10 dimethicone, or a combination thereof Nonlimiting examples of non-sulfate anionic surfactants include acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof. In a preferred embodiment, at least one of the one or more non-sulfate anionic surfactants is an alkyl sulfonate. Nonlimiting examples of alkyl sulfonates include $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium $C_{14}$-$C_{16}$ olefin sulfonate, or a combination thereof.

Non-limiting examples of amphoteric surfactants include alkyl amphoproprionates, betaines, alkyl sultaines, alkyl amphoacetates, salts thereof, and a combination thereof. In various embodiments, one or more betaines are particularly useful. Nonlimiting examples of betaines include cocamidopropyl betaine, coco betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, salts thereof, or combinations thereof.

Non-limiting examples of nonionic surfactants include polyols with fatty acids (such as glycerol esters), alkyl polyglucosides, alkanolamides, polyoxyalkylenated nonionic surfactants, polyglycerolated nonionic surfactants, ethoxylated fatty esters, and a combination thereof. In some instances, a plurality of nonionic surfactants are particularly useful.

Non-limiting examples of cationic polymers include copolymers of 1-vinyl-2-pyrrolidine and 1-vinyl-3-methylimidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). Additionally, or alternatively, the cationic conditioning polymers may include or be chosen from cationic guar gum derivatives, such as guar hydroxypropyltrimonium chloride.

Many additional components may optionally be included in (or excluded from) the cleansing compositions, for example, water-soluble solvents other than propylene glycol, thickening agents, non-silicone fatty compounds, silicones including amino-functionalized silicones, additional conditioning agents, and/or miscellaneous ingredients, such preservatives, colorants, pH modifying agents, chelating agents, film-forming polymers, etc.

The cleansing compositions are particularly useful for cleansing and conditioning hair. The compositions exhibit good cleansing ability, lather, foaming and foam stability, and conditioning properties. Additionally, the cleansing compositions are particularly well-suited for cleansing artificially colored hair because the compositions preserve the color of the artificially colored hair while simultaneously providing shine, smoothness, moisturization, and a pleasant tactile film to hair.

DETAILED DESCRIPTION OF THE DISCLOSURE

The cleansing compositions of the instant case are free or essentially free from sulfate-based surfactants yet provide good cleansing ability without stripping desirable oils from the skin and hair. The compositions are particularly useful for cleansing artificially colored hair because they have a preserving influence on the hair, i.e., they do not appreciably remove the artificial color from the hair. In addition, they impart shine, smoothness, moisturization, and a pleasant tactile feel to the hair. Despite including higher than typical amounts of non-sulfate anionic surfactants and cationic conditioning polymers, the compositions are stable. The cleansing compositions typically include:

- (a) about 0.1 to about 4 wt. % of one or more PEG/PPG dimethicones;
- (b) at least 0.5 to about 10 wt. % of propylene glycol;
- (c) about 10 to about 25 wt. % of a plurality of surfactants, the plurality of surfactants comprising:
  - (c)(i) one or more non-sulfate based anionic surfactants;
  - (c)(ii) one or more amphoteric surfactants; and
  - (c)(iii) one or more nonionic surfactants;
- (d) one or more cationic conditioning polymers;
- (e) optionally, about 0.1 to about 15 wt. % of one or more water-soluble solvents, other than propylene glycol; and
- (f) about 60 to about 85 wt. % of water;
  - wherein all weight percentages are based on the total weight of the composition; and wherein the composition is free or essentially free from sulfate-based surfactants.

The cleansing compositions is typically an oil-in-water emulsion or dispersion. Due to the cleansing and conditioning properties of the cleansing compositions, the cleansing composition may be designated as a "shampoo," a "conditioning shampoo," or an "all-in-one conditioning and shampooing composition." The cleansing compositions may also be a body wash or both a hair and body wash.

(a) PEG/PPG-Dimethicones

The PEG/PPG dimethicones useful in the cleansing compositions include, but are not limited to, those having from 3 to 30 ethoxy units and from 3 to 30 propoxy units. Nonlimiting examples include PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 Dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone, PEG/PPG-27/27, bis-PEG/PPG 18/6 dimethicone, PEG/PPG 30/10 dimethicone, or combinations thereof. In various embodiments, the one or more PEG/PPG-dimethicones are selected from PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, or combinations thereof. A particularly suitable PEG/PPG-dimethicone is PEG/PPG-4/12 dimethicone.

The total amount of the one or more PEG/PPG-dimethicones will vary. Nonetheless, in various embodiments, the cleansing composition includes about 0.1 to about 5 wt. % of the one or more PEG/PPG dimethicones, based on a total weight of the cleansing composition. In further embodiments, the cleansing composition includes about 0.1 to about 4 wt. %, about 0.1 to about 3 wt. %, about 0.1 to about 2 wt. %, about 0.1 to about 1 wt. %, about 0.2 to about 5 wt. %, about 0.2 to about 4 wt. %, about 0.2 to about 3 wt. %, about 0.2 to about 2 wt. %, or about 0.2 to about 1 wt. % of the one or more PEG/PPG-dimethicones, based on a total weight of the cleansing composition.

(b) Propylene Glycol

Propylene glycol is a viscous, colorless liquid, which is nearly odorless but possesses a faintly sweet taste. Its chemical formula is $CH_3CHCH_2OH$. Containing two alcohol groups, it is classed as a diol. The total amount of the propylene glycol in the cleansing compositions will vary. Nonetheless, in various embodiments, the cleansing composition includes at least 0.4 wt. % of propylene glycol, for example, about 0.5 to about 15 wt. % of propylene glycol, based on a total weight of the cleansing composition. In further embodiments, the cleansing composition includes about 0.5 to about 12 wt. %, about 0.5 to about 10 wt. %, about 0.5 to about 8 wt. %, about 0.5 to about 5 wt. %, about 0.5 to about 3 wt. %, about 0.8 to about 15 wt. %, about 0.8 to about 12 wt. %, about 0.8 to about 10 wt. %, about 0.8 to about 8 wt. %, about 0.8 to about 5 wt. %, about 0.8 to about 3 wt. %, about 1 to about 15 wt. %, about 1 to about 12 wt. %, about 1 to about 10 wt. %, about 1 to about 8 wt. %, about 1 to about 5 wt. %, about 1 to about 3 wt. %, at least 1 to about 15 wt. %, at least 1 to about 12 wt. %, at least 1 to about 10 wt. %, at least 1 to about 8 wt. %, at least 1 to about 5 wt. %, at least 1 to about 3 wt. %, based on a total weight of the cleansing composition.

Ratio of (a) to (b)

The weight ratio of the one or more PEG/PPG-dimethicones of (a) to the propylene glycol of (b) will vary. Nonetheless, in various embodiments, (a) and (b) are in a weight ratio of about 1:2 to about 1:20 ((a):(b)). In further embodiments, (a) and (b) are in a weight ratio of about 1:2 to about 1:18, about 1:2 to about 1:15, about 1:2 to about 1:12, about 1:2 to about 1:10; about 1:2 to about 1:8, about 1:2 to about 1:7, about 1:3 to about 1:20, about 1:3 to about 1:18, about 1:3 to about 1:15, about 1:3 to about 1:12, about 1:3 to about 1:10, about 1:3 to about 1:8, or about 1:3 to about 1:7.

(c) Plurality of Surfactants

The cleansing compositions include one or more non-sulfate anionic surfactants, one or more amphoteric surfactants, and one or more nonionic surfactants. The non-sulfate anionic surfactants, the amphoteric surfactants, and the nonionic surfactants interact to form a surfactant system that imparts cleansing ability, stability, lathering, and foaming properties to the cleansing compositions. Anionic surfactants carry a negative charge on the polar head group. These surfactants are typically used for their detergency properties. They are highly effective at removing dirt and oil from the body, hair, and scalp. Nonionic surfactants have no (or little) residual electric charge. These surfactants can perform a variety of functions, such as emulsion stabilization, mild detergency, and viscosity modification. Amphoteric (zwitterionic) surfactants are dual-charged (having both a positive and negative charge on the molecule). Many amphoteric surfactants display pH-dependent charge behavior, having one charge at a lower pH and the opposite charge at a higher pH. These types of surfactants tend to be mild both to skin and hair. They can also provide foam-boosting properties in combination with anionic surfactants, which enhances lather.

The total amount of the plurality of surfactants in the cleansing composition will vary. Nonetheless, in various embodiments, the cleansing composition includes about 10 to about 30 wt. % of the plurality of surfactants, based on a total weight of the cleansing composition. In further embodiments, the cleansing composition includes about 10 to about 25 wt. %, about 10 to about 20 wt. %, about 12 to about 30 wt. %, about 12 to about 25 wt. %, about 12 to about 20 wt. %, about 15 to about 30 wt. %, about 15 to about 25 wt. %, or about 15 to about 20 wt. %, based on a total weight of the cleansing composition.

In various embodiments, the total amount of the one or more non-sulfate anionic surfactants of (a) is greater than the total amount of the one or more amphoteric surfactants of (b); and the total amount of the one or more nonionic surfactants of (c) is greater than the total amount of the one or more amphoteric surfactants of (b), i.e., (a)>(b)<(c). As explained in more detail later, in certain embodiments, the total amount of the one or more anionic surfactants of (a) is greater than the total combined amount of the one or more amphoteric surfactants of (b) and the one or more nonionic surfactants of (c), i.e., (a)>((b)+(c)).

(c)(i) Non-Sulfate Anionic Surfactants

In some instances, the non-sulfate anionic surfactant(s) are the predominant type of surfactant in the cleansing composition (i.e., there is a higher percentage of non-sulfate anionic surfactant(s) than any other single surfactant type in the cleansing composition). Moreover, in some instances, the total amount of non-sulfate anionic surfactants in the cleansing composition is higher than the total amount of all other surfactant types in the cleansing composition. In other words, the phrase "all other surfactants" means any and all surfactants in the cleansing composition other than non-sulfate anionic surfactants.

Useful non-sulfate anionic surfactants include, but are not limited to, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof. More detailed descriptions and non-limiting examples of useful non-sulfate anionic surfactants are provided below.

Acyl Isethionates

Non-limiting examples of useful acyl isethionates include those of formula (I) and (I)

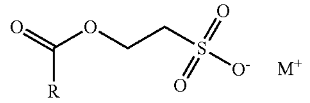

(II)

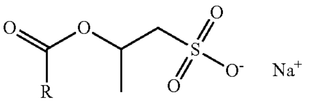

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some instances, sodium cocoyl methyl isethionate is a particularly useful acyl isethionate that may be included in the cleansing compositions.

The total amount of the one or more acyl isethionates in the cleansing composition, if present, may vary but is typically from about 0.01 to about 15 wt. %, based on the total weight of the cleansing composition. In some instance, the total amount of the one or more acyl isethionates in the cleansing composition is from about 0.01 to about 10 wt. %, about 0.01 to about 5 wt. %, about 0.1 to about 15 wt. %, about 0.1 to about 10 wt. %, about 0.1 to about 8 wt. %, about 1 to about 15 wt. %, about 1 to about 10 wt. %, or about 1 to about 8 wt. %, about 1 to about 5 wt. %, about 1 to about 3 wt. %, based on the total weight of the cleansing composition.

In another embodiment, the total amount of the one or more acyl isethionates in the cleansing composition, if present, is from about 5 to about 15 wt. %, about 5 to about 12 wt. %, or about 5 to about 10 wt. %, based on the total weight of the cleansing composition.

Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (III):

(III)

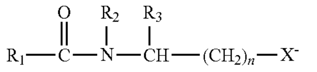

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. In some cases one or more acyl sarcosinates are preferred.

Acyl Sarcosinates

In a preferred embodiment, the cleansing composition of the instant case includes one or more acyl sarcosinates. Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred.

The total amount of the one or more acyl sarcosinates in the cleansing composition, if present, may vary but is typically from about 0.01 to about 15 wt. %, based on the total weight of the cleansing composition. In some instance, the total amount of the one or more acyl sarcosinates in the cleansing composition is from about 0.01 to about 10 wt. %, about 0.01 to about 5 wt. %, about 0.1 to about 15 wt. %, about 0.1 to about 10 wt. %, about 0.1 to about 8 wt. %, about 1 to about 15 wt. %, about 1 to about 10 wt. %, or about 1 to about 8 wt. %, about 1 to about 5 wt. %, about 1 to about 3 wt. %, based on the total weight of the cleansing composition.

In another embodiment, the total amount of the one or more acyl sarcosinates in the cleansing composition, if present, is from about 5 to about 15 wt. %, about 5 to about 12 wt. %, or about 5 to about 10 wt. %, based on the total weight of the cleansing composition.

Acyl Taurates

Non-limiting examples of acyl taurates include those of formula (IV):

(IV)

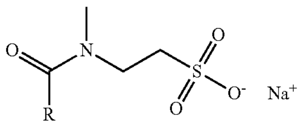

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts include sodium cocoyl taurate and sodium methyl cocoyl taurate.

The total amount of the one or more acyl taurates in the cleansing composition, if present, may vary but is typically from about 0.01 to about 15 wt. %, based on the total weight of the cleansing composition. In some instance, the total amount of the one or more acyl taurates in the cleansing composition is from about 0.01 to about 10 wt. %, about 0.01 to about 5 wt. %, about 0.1 to about 15 wt. %, about 0.1 to about 10 wt. %, about 0.1 to about 8 wt. %, about 1 to about 15 wt. %, about 1 to about 10 wt. %, or about 1 to about 8 wt. %, about 1 to about 5 wt. %, about 1 to about 3 wt. %, based on the total weight of the cleansing composition.

In another embodiment, the total amount of the one or more acyl taurates in the cleansing composition, if present, is from about 5 to about 15 wt. %, about 5 to about 12 wt. %, or about 5 to about 10 wt. %, based on the total weight of the cleansing composition.

Acyl Glycinates

Non-limiting examples of useful acyl glycinates include those of formula (V):

(V)

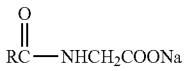

wherein R is an alkyl chain of 8 to 16 carbon atoms. Sodium is shown as the cation in the above formula (X) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of the one or more acyl glycinates in the cleansing composition, if present, may vary but is typically from about 0.01 to about 15 wt. %, based on the total weight of the cleansing composition. In some instance, the total amount of the one or more acyl glycinates in the cleansing composition is from about 0.01 to about 10 wt. %, about 0.01 to about 5 wt. %, about 0.1 to about 15 wt. %, about 0.1 to about 10 wt. %, about 0.1 to about 8 wt. %, about 1 to about 15 wt. %, about 1 to about 10 wt. %, or about 1 to about 8 wt. %, about 1 to about 5 wt. %, about 1 to about 3 wt. %, based on the total weight of the cleansing composition.

In another embodiment, the total amount of the one or more acyl glycinates in the cleansing composition, if present, is from about 5 to about 15 wt. %, about 5 to about 12 wt. %, or about 5 to about 10 wt. %, based on the total weight of the cleansing composition.

Acyl Glutamates

Non-limiting examples of useful acyl glutamates include those of formula (VI):

(VI)

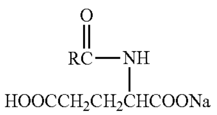

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of the one or more acyl glutamates in the cleansing composition, if present, may vary but is typically from about 0.01 to about 15 wt. %, based on the total weight of the cleansing composition. In some instance, the total amount of the one or more acyl glutamates in the cleansing composition is from about 0.01 to about 10 wt. %, about 0.01 to about 5 wt. %, about 0.1 to about 15 wt. %, about 0.1 to about 10 wt. %, about 0.1 to about 8 wt. %, about 1 to about 15 wt. %, about 1 to about 10 wt. %, or about 1 to about 8 wt. %, about 1 to about 5 wt. %, about 1 to about 3 wt. %, based on the total weight of the cleansing composition.

In another embodiment, the total amount of the one or more acyl glutamates in the cleansing composition, if present, is from about 5 to about 15 wt. %, about 5 to about 12 wt. %, or about 5 to about 10 wt. %, based on the total weight of the cleansing composition.

Alkyl Sulfonates

Useful alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (VII) is particularly useful.

(VII)

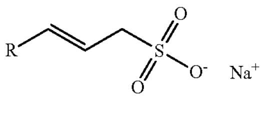

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium $C_{14-16}$ olefin sulfonate.

In a preferred embodiment, at least one of the one or more non-sulfate anionic surfactants is an alkyl sulfonate. For example, in certain embodiments, the cleansing composition includes about 1 to about 25 wt. % of the one or more alkyl sulfonates. In further embodiments, the cleansing composition includes about 1 to about 20 wt. %, about 1 to about 15 wt. %, about 1 to about 12 wt. %, about 1 to about 10 wt. %, about 1 to about 5 wt. %, about 2 to about 25 wt. %, about 2 to about 20 wt. %, about 2 to about 15 wt. %, about 2 to about 12 wt. %, about 2 to about 10 wt. %, about 2 to about 8 wt. %, about 5 to about 25 wt. %, about 5 to about 20 wt. %, about 5 to about 15 wt. %, about 5 to about 12 wt. %, about 5 to about 10 wt. %, about 8 to about 25 wt. %, about 8 to about 20 wt. %, about 8 to about 15 wt. %, about 8 to about 12 wt. %, about 8 to about 25 wt. %, about 8 to about 20 wt. %, about 8 to about 18 wt. %, about 8 to about 15 wt. %, or about 8 to about 12 wt. % of the one or more alkyl sulfonates, based on a total weight of the cleansing composition.

Alkyl Sulfosuccinates

Non-limiting examples of useful sulfosuccinates include those of formula (VIII):

(VIII)

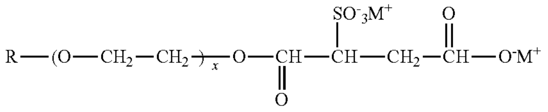

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a combination thereof. In some instances, disodium laureth sulfosuccinate is particularly preferred.

The total amount of alkyl sulfosuccinates in the cleansing composition, if present, may vary but is typically from about 0.01 to about 15 wt. %, based on the total weight of the cleansing composition. In some instance, the total amount of alkyl sulfosuccinates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, about 5 to about 15 wt. %, about 5 to about 12 wt. %, or about 5 to about 10 wt. %, based on the total weight of the cleansing composition.

Alkyl Sulfoacetates

Non-limiting examples of alkyl sulfoacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of alkyl sulfoacetates in the cleansing composition, if present, may vary but is typically from about 0.01 to about 15 wt. %, based on the total weight of the cleansing composition. In some instance, the total amount of alkyl sulfoacetates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, about 1 to about 5 wt. %, about 5 to about 15 wt. %, about 5 to about 12 wt. %, or about 5 to about 10 wt. %, based on the total weight of the cleansing composition.

Alkoxylated Monoacids

Non-limiting examples of alkoxylated monoacids include compounds corresponding to formula (IX):

$$RO[CH_2O]_u[(CH_2)_xCH(R')(CH_2)_y(CH_2)_zO]_v[CH_2CH_2O]_wCH_2COOH \quad (IX)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z>0;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

The total amount of alkoxylated monoacids in the cleansing composition, if present, may vary but is typically from about 0.01 to about 15 wt. %, based on the total weight of the cleansing composition. In some instance, the total amount of alkoxylated monoacids in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, about 1 to about 5 wt. %, about 5 to about 15 wt. %, about 5 to about 12 wt. %, or about 5 to about 10 wt. %, based on the total weight of the cleansing composition.

In a preferred embodiment, the cleansing composition includes two or more non-sulfate anionic surfactants selected from acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof. In an embodiment, at least one of the two or more anionic surfactants is an alkyl sulfonate, an acyl amino acid, salts thereof, or a combination thereof. In an embodiment, at least one of the two or more anionic surfactants is an alkyl sulfonate, an acyl sarcosinate, or a combination thereof. In a preferred embodiment, the cleansing composition include one or more alkyl sulfonates and one or more amino acid surfactants selected from acyl taurates, acyl glycinates, acyl glutamates, and acyl sarcosinates, wherein acyl sarcosinates are preferred.

The total amount of all non-sulfate anionic surfactants in the cleansing compositions will vary. Nonetheless, in various embodiments, the cleansing composition includes about 5 to about 35 wt. % of the one or more non-sulfate anionic surfactants. In further embodiments, the hair cleansing composition includes about 5 to about 30 wt. %, about 5 to about 25 wt. %, about 5 to about 22 wt. %, about 5 to about 20 wt. %, about 8 to about 35 wt. %, about 8 to about 30 wt. %, about 8 to about 25 wt. %, about 8 to about 22 wt. %, about 8 to about 20 wt. %, about 10 to about 35 wt. %, about 10 to about 30 wt. %, about 10 to about 25 wt. %, about 10 to about 22 wt. %, about 10 to about 20 wt. %, about 12 to about 35 wt. %, about 12 to about 30 wt. %, about 12 to about 25 wt. %, about 12 to about 22 wt. %, about 12 to about 20 wt. %, 15 to about 30 wt. %, about 15 to about 25 wt. %, about 15 to about 22 wt. %, or about 15 to about 20 wt. % of the one or more non-sulfate anionic surfactants, based on a total weight of the cleansing composition.

(c)(ii) Amphoteric Surfactants

Nonlimiting examples of amphoteric surfactants include alkyl amphoproprionates, betaines, alkyl sultaines, alkyl amphoacetates, and combinations thereof. In some instances, it is preferable to include one or more alkyl betaines.

The total amount of the one or more amphoteric surfactant(s) in the cleansing compositions will vary but is typically from about 0.1 to about 15 wt. %, based on the total weight of the cleansing composition. In some instance, the total amount of the one or more amphoteric surfactants in the cleansing composition is from about 0.1 to about 10 wt. %, from about 0.1 to about 8 wt. %, about 0.1 to about 5 wt. %, about 0.1 to about 3 wt. %, about 1 to about 15 wt. %, about 1 to about 10 wt. %, about 1 to about 8 wt. %, about 1 to about 5 wt. %, about 1 to about 3 wt. %, about 2 to about 15 wt. %, about 2 to about 10 wt. %, or about 2 to about 8 wt. %, about 2 to about 5 wt. %, or about 2 to about 4 wt. %, based on the total weight of the cleansing composition.

Alkyl Amphopropionates

In some instances, the cleansing compositions preferably include one or more alkyl amphopropionates. Non-limiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof. Sodium cocoamphopropionate is a particularly useful alkyl amphopropionate that can be included in the cleansing compositions.

The total amount of alkyl amphopropionates in the cleansing composition, if present, may vary but is typically from about 0.01 to about 15 wt. %, based on the total weight of the cleansing composition. In some instance, the total amount of amphopropionates in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Betaines

Useful betaines include those of the following formulae (Xa-Xd):

(Xa)

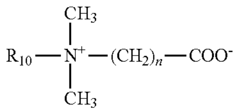

(Xb)

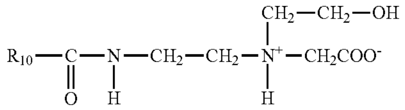

(Xc)

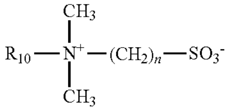

-continued (Xd)

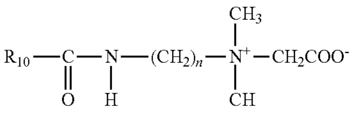

wherein $R_{10}$ is an alkyl group having 8-18 carbon atoms; and n is an integer from 1 to 3.

Particularly useful betaines include, for example, coca betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Typically, at least one betaine compound is selected from coco betaine, cocamidopropyl betaine, behenyl betaine, capryl/capramidopropyl betaine, and lauryl betaine, and combinations thereof. Particularly preferred betaines include coco betaine and cocamidopropyl betaine.

In a preferred embodiment, the cleansing composition includes at least one betaine, preferably at least two betaines.

The total amount of the one or more betaines in the cleansing composition, if present, may vary but is typically from about 0.01 to about 15 wt. %, based on the total weight of the cleansing composition. In some instance, the total amount of the one or more betaines in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Alkyl Sultaines

Non-limiting examples of alkyl sultaines include hydroxyl sultaines of formula (XI)

(XI)

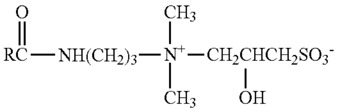

wherein R is an alkyl group having 8-18 carbon atoms. More specific examples include, but are not limited to cocamidopropyl hydroxysultaine, lauryl hydroxysultaine, and a combination thereof.

The total amount of the one or more alkyl sultaines in the cleansing composition, if present, may vary but is typically from about 0.01 to about 15 wt. %, based on the total weight of the cleansing composition. In some instance, the total amount of the one or more alkyl sultaines in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Alkyl Amphoacetates and Alkyl Amphodiacetates

Useful alkyl amphoacetates and alkyl amphodiacetates include those of Formula (XI) and (XII):

(XI)

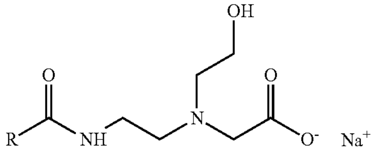

(XII)

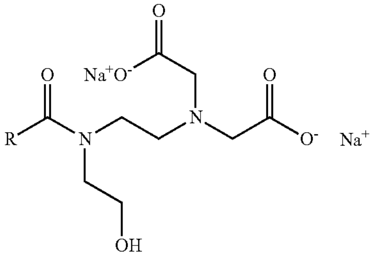

wherein R is an alkyl group having 8-18 carbon atoms. Sodium is shown as the cation in the formulae above, but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of alkyl amphoacetates and/or alkyl amphodiacetates in the

The total amount of the one or more alkyl amphoacetates and/or alkyl amphodiacetates in the cleansing composition, if present, may vary but is typically from about 0.01 to about 15 wt. %, based on the total weight of the cleansing composition. In some instance, the total amount of the one or more alkyl amphoacetates and/or alkyl amphodiacetates in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

(c)(iii) Nonionic Surfactants

The cleansing compositions include one or more nonionic surfactants, preferably a plurality of nonionic surfactants. Non-limiting examples of nonionic surfactants include: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides; and combinations thereof.

The total amount of the one or more nonionic surfactants in the cleansing composition will vary. Nonetheless, in certain embodiments, the total amount of the one or more nonionic surfactants in the cleansing composition is from about 0.1 to about 15 wt. %, based on the total weight of the cleansing composition. In some instances, the total amount of the one or more nonionic surfactants is about 0.1 to about 12 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 12 wt. %, about 1 to about 10 wt. %, about 1 to about 8 wt. %, about 2 to about 15 wt. %, about 2 to about 12 wt. %, about 2 to about 10 wt. %, about 2 to about 8 wt. %, about 3 to about 15 wt. %, about 3 to about 12 wt. %, about 3 to about 10 wt. %, or about 3 to about 8 wt. %, based on a total weight of the cleansing composition.

Alkanolamides

Non-limiting examples alkanolamides include fatty acid alkanolamides. The fatty acid alkanolamides may be fatty acid monoalkanolamides, fatty acid dialkanolamides, or fatty acid isoalkanolamides, and may have a $C_{2-8}$ hydroxyalkyl group (the $C_{2-8}$ chain can be substituted with one or more than one-OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and combinations thereof.

In some instances, the fatty acid alkanolamides preferably include cocamide MIPA, cocamide DEA, cocamide MEA, cocamide DIPA, and combinations thereof. In particular, the fatty acid alkanolamide may be cocamide MIPA, which is commercially available under the tradename “EMPILAN” from Innospec Active Chemicals.

Fatty acid alkanolamides include those of the following structure:

(XIII)

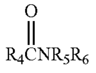

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and combinations thereof);

$R_6$ is selected from —$CH_2OH$, —$CH_2CH_2OH$, —$CH_2CH_2CH_2OH$, —$CH_2(CHOH)_4CH_2OH$, -benzyl, and combinations thereof;

$R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and combinations thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

The total amount of one or more alkanolamides in the cleansing compositions, if present, can vary but is typically about 0.1 to about 15 wt. %, based on the total weight of the cleansing composition. In some instances, the total amount of the one or more alkanolamides is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

Alkyl Polyglucosides

Useful alkyl polyglucosides include those having the following formula (XIV):

$$R^1—O—(R^2O)_n—Z(x) \quad \text{(XIV)}$$

wherein $R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Useful alkyl poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

The total amount of the one or more alkyl polyglucosides in the cleansing compositions, if present, can vary but is typically about 0.0 to about 15 wt. %, based on the total weight of the cleansing compositions. In some instances, the total amount of the one or more alkyl polyglucosides is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

Additional Nonionic Surfactants

Nonionic surfactants also include, for example, alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides; and combinations thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and combinations thereof.

Examples of ethoxylated fatty esters that may be mentioned include the adducts of ethylene oxide with esters of lauric acid, palmitic acid, stearic acid or behenic acid, and combinations thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and combinations thereof.

As glyceryl esters of fatty acids, glyceryl stearate (glyceryl mono-, di- and/or tristearate) (CTFA name: glyceryl stearate) or glyceryl ricinoleate and combinations thereof can in particular be used.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be used.

Mixtures of these surfactants, such as for example the product containing glyceryl stearate and PEG-100 stearate, marketed under the name "ARLACEL 165" by Uniqema, and the product containing glyceryl stearate (glyceryl mono- and distearate) and potassium stearate marketed under the name "TEG1N" by Goldschmidt (CTFA name: glyceryl stearate SE), can also be used.

The total amount of additional nonionic surfactants (nonionic surfactants other than alkanolamides and alkyl polyglucosides) in the cleansing compositions, if present, can vary but is typically about 0.1 to about 15 wt. %, based on the total weight of the cleansing composition. In some instances, the total amount of additional nonionic surfactants is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

(d) Cationic Conditioning Polymers

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a combination thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus, when the polymer is not a homopolymer, it can contain spacer noncationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary, or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$ alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the "LUVIQUAT" tradename (e.g., "LUVIQUAT FC 370"); copolymers of 1-vinyl-2-pyrrolidine and dimethylaminoethyl methacrylate (referred to as "Polyquaternium-11") such as those commercially from Gar Corporation (Wayne, N.J., USA) under the "GAFQUAT" tradename (e.g., "GAFQUAT 755N"); and cationic diallyl quaternary ammonium-containing polymer including, for example, dimethyldiallyammonium chloride homopolymer and copolymers of acrylamide and dimethyldiallyammonium chloride (referred to as "Polyquaternium-6" and "Polyquaternium-7").

Other cationic conditioning polymers that can be used include polysaccharide polymers, such as cationic cellulose derivatives and cationic starch derivatives. Cationic cellulose is available from Amerchol Corp. (Edison, N.J., USA) in its "Polymer JR" (trademark) and "Polymer LR" (trade mark) series of polymers, as salts of hydroxyethyl cellulose reacted with trimethyl ammonium substituted epoxide (referred to as "Polyquaternium-10"). Another type of cationic cellulose includes the polymeric quaternary ammonium salts of hydroxyethyl cellulose reacted with lauryl dimethyl ammonium-substituted epoxide (referred to as "Polyquaternium-24"). These materials are available from Amerchol Corp. (Edison, N.J., USA) under the tradename "Polymer LM-200."

Other cationic conditioning polymers that can be used include cationic guar gum derivatives, such as guar hydroxypropyltrimonium chloride or hydroxypropyl guar hydroxypropyltrimmonium chloride.

Polyquaterniums include Polyquaternium-1 (ethanol, 2,2', 2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N, N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene (dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine) methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some instances, the cleansing compositions of the instant disclosure include one or more cationic conditioning polymers selected from cationic cellulose derivatives, quaternized hydroxyethyl cellulose (e.g., polyquaternium-10), cationic starch derivatives, cationic guar gum derivatives (guar hydroxypropyltrimonium chloride or hydroxypropyl guar hydroxypropyltrimmonium chloride), copolymers of acrylamide and dimethyldiallyammonium chloride (e.g., polyquaternium-7), polyquaterniums, and a combination thereof. In one particularly preferred embodiment, the cationic conditioning polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a combination thereof. In particular, polyquaternium-7 and/or polyquaternium-10 can be particularly useful.

The total amount of cationic conditioning polymers can vary. Nonetheless, in various embodiments, the cleansing composition includes about 0.01 to about 10 wt. % of the one or more cationic conditioning polymers, based on a total weight of the cleansing composition. In some cases, the total amount of the cationic conditioning polymers is about 0.01 to about 5 wt. %, about 0.01 to about 3 wt. %, about 0.01 to about 2 wt. %, about 0.01 to about 1 wt. %, about 0.05 to about 10 wt. %, about 0.05 to about 5 wt. %, about 0.05 to about 3 wt. %, about 0.05 to about 2 wt. %, about 0.05 to about 1 wt. %, about 0.1 to about 5 wt. %, or about 0.1 to about 3 wt. %, or about 0.1 to about 2 wt. %, about 0.1 to about 1 wt. %, based on the total weight of the cleansing composition.

(e) Water-Soluble Solvent Other than Propylene Glycol

The term “water soluble organic solvent” is interchangeable with the terms “water soluble solvent” and “water-miscible solvent” and means a compound that is liquid at 25° C. and at atmospheric pressure (760 mmHg), and it has a solubility of at least 50% in water under these conditions. In some cases, the water-soluble solvents have a solubility of at least 60%, 70%, 80%, or 90%. Non-limiting examples of water-soluble solvents include, for example, organic solvents selected from glycerin, alcohols (for example, $C_{1-12}$, $C_{1-10}$, $C_{1-8}$, or $C_{1-4}$ alcohols), polyols (polyhydric alcohols), glycols, and a combination thereof.

Non-limiting examples of water soluble organic solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, ethers of propylene glycol, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, butylene glycol, hexylene glycol, propane diol, and glycerin. The organic solvents can be volatile or non-volatile compounds.

Further non-limiting examples of water soluble organic solvents include alkanediols (polyhydric alcohols) such as glycerin, 1,2,6-hexanetriol, trimethylolpropane, ethylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a combination thereof.

Polyhydric alcohols are useful. Examples of polyhydric alcohols include glycerin, ethylene glycol, diethylene glycol, triethylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a combination thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a combination thereof.

The amount of the one or more water soluble solvents in the cleansing composition, if present, will vary. Nonetheless, in various embodiments, the cleansing composition includes about 0.1 to about 10 wt. % of the one or more water soluble organic solvents other than propylene glycol, based on a total weight of the hair styling composition. In further embodiments, the cleansing composition includes about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 1 to about 10 wt. %, about 1 to about 8 wt. %, about 1 to about 6 wt. %, or about 1 to about 5 wt. % of the one or more water soluble organic solvents other than propylene glycol, based on a total weight of the hair styling composition.

(f) Water

The total amount of water in the cleansing compositions can vary. Nonetheless, in various embodiments, the cleansing composition includes about 50 to about 85 wt. % of water, based on a total weight of the cleansing composition. In further embodiments, the cleansing composition includes about 50 to about 82 wt. %, about 50 to about 80 wt. %, about 55 to about 85 wt. %, about 55 to about 82 wt. %, about 55 to about 80 wt. %, about 60 to about 85 wt. %, about 60 to about 82 wt. %, about 60 to about 80 wt. %, about 65 to about 85 wt. %, about 65 to about 82 wt. %, about 65 to about 80 wt. %, about 70 to about 85 wt. %, about 70 to about 82 wt. %, about 70 to about 80 wt. % of water, based on a total weight of the cleansing composition.

(g) Thickening Agent

The cleansing compositions may optionally include one or more thickening agents (also referred to as thickeners or viscosity modifying agents). Many thickening agents are water-soluble and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

The total amount of the one or more thickening agents in the cleansing compositions, if present, may vary but is typically in an amount of from about 0.01 to about 10 wt. %, from based on the total weight of the cleansing composition. In some instances, the total amount of thickening agent in the cleansing composition is from about 0.01 to about 5 wt. %, from about 0.01 to about 3 wt. %, from about 0.05 to about 10 wt. %, from about 0.05 to about 5 wt. %, from about 0.05 to about 3 wt. %, about 0.05 to about 2 wt. %, about 0.05 to about 1 wt. %, from about 0.1 to about 10 wt. %, from about 0.1 to about 5 wt. %, or from about 0.1 to about 3 wt. %, about 0.1 to about 2 wt. %, or about 0.1 to about 1 wt. % of the one or more thickening agents, based on the total weight of the cleansing composition.

Non-limiting examples of thickening agents include xanthan gum, guar gum, biosaccharide gum, cellulose, acacia Seneca gum, *sclerotium* gum, agarose, pectin, gellan gum, and hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some instances, the thickening agent(s) are selected from carboxylic acid polymers (e.g., carbomer), crosslinked polyacrylate polymers, polyacrylamide polymers, polysaccharides, gums, and a combination thereof. Carbomer is a particularly useful and preferred thickening agent.

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the "Carbopol.® 900" series from B.F. Goodrich (e.g., "Carbopol® 954"). In addition, other suitable carboxylic acid polymeric agents include "Ultrez® 10" (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as "Carbopol® 1342," "Carbopol® 1382," "Pemulen TR-1", and "Pemulen TR-2" from B.F. Goodrich. In other words, examples of carboxylic acid polymer thickeners useful herein are those selected from carbomers, acrylates/C10-C30 alkyl acrylate crosspolymers, and combinations thereof. Further nonlimiting examples of thickening agents include crosslinked polyacrylate polymers, polyacrylamide polymers, polysaccharides, and gums, as set forth below.

Crosslinked Polyacrylate Polymers

The compositions of the present disclosure can optionally contain crosslinked polyacrylate polymers useful as thickeners or gelling agents including both cationic and nonionic polymers.

Polyacrylamide Polymers

The compositions of the present disclosure can optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the tradename "Sepigel 305" from Seppic Corporation.

Other polyacrylamide polymers useful herein include multi-block copolymers of acrylamides and substituted acrylamides with acrylic acids and substituted acrylic acids. Commercially available examples of these multi-block copolymers include "Hypan SR150H," "Hypan SS500V," Hypan SS500W", and "Hypan SSSA100H" from Lipo Chemicals, Inc.

The compositions may also contain thickening and texturizing gels of the type as exemplified by the product range called "Lubrajel®" from United Guardian. These gels have moisturizing, viscosifying, and stabilizing properties.

Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename "Natrosol® CS Plus" from Aqualon Corporation.

Other useful polysaccharides include scleroglucans comprising a linear chain of (1-3) linked glucose units with a (1-6) linked glucose every three units, a commercially available example of which is "Clearogel™ CS11" from Michel Mercier Products Inc.

Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosaccharide gum, and combinations thereof.

Additional examples of water-soluble thickeners include water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, and hydroxypropyl starch).

(h)(i) Silicones Other than the PEG/PPG-Dimethicones of (a)

Nonlimiting examples of silicones other than the PEG/PPG-Dimethicones of (a) include, but are not limited to, polyorganosiloxanes, polyalkylsiloxanes, polyarylsiloxanes, polyalkarylsiloxanes, polyestersiloxanes, and a combination thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane, and a combination thereof.

In some instances, the cleansing compositions include one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and combinations thereof. Particularly preferred silicones include dimethicone, amodimethicone, and a combination thereof.

The cleansing compositions may include one or more silicone oils, for example one or more non-phenyl silicone oils and/or one or more phenyl silicone oils. The silicone oil is preferably apolar. An "apolar silicone oil" is intended to denote a silicone oil that does not comprise ionic or ionizable group(s) to a significant degree, and preferably does not comprise any oxyalkylenated ($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

- polydimethylsiloxanes (PDMSs),
- PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference "ABIL WAX 9801" from Evonik Goldschmidt,
- PDMSs comprising aliphatic groups, or functional groups such as hydroxyl, thiol and/or amine groups, [
- polyalkylmethylsiloxanes substituted with functional groups such as hydroxyl, thiol and/or amine groups,
- polysiloxanes modified with fatty acids, fatty alcohols or polyoxyalkylenes, and combinations thereof.

Preferably, these non-volatile non-phenyl silicone oils are chosen from polydimethylsiloxanes; alkyl dimethicones; and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of the following formula (XV):

(XV)

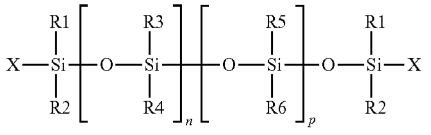

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular of which the viscosity at 25° C. is between 9 centistokes (cSt) and 800 000 (cSt).

As non-volatile non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name "SE30" by the company General Electric, the product sold under the name "AK 500000" by the company Wacker, the product sold under the name "Mirasil DM 500 000" by the company Bluestar, and the product sold under the name "Dow Corning 200 Fluid 500 000 cSt" by the company Dow Corning, the substituents $R_1$ to $R_6$ and X represent a methyl group, and p and n are such that the viscosity is 60 000 cSt, for example the product sold under the name "Dow Corning 200 Fluid 60 000 CS" by the company Dow Corning, and the product sold under the name "Wacker Belsil DM 60 000" by the company Wacker, the substituents $R_1$ to $R_6$ and X represent a methyl group, and p and n are such that the viscosity is 100 cSt or 350 cSt, for example the products sold respectively under the names "Belsil DM100" and "Dow Corning 200 Fluid 350 CS" by the company Dow Corning, the substituents $R_1$ to $R_6$ represent a methyl group, the group X represents a hydroxyl group, and n and p are such that the viscosity is 700 cSt, for example the product sold under the name "Baysilone Fluid T0.7."

The total amount of silicones in the cleansing compositions will vary. Nonetheless, in various embodiments, the cleansing composition include about 0.1 to about 10 wt. % of one or more silicones other than the PEG/PPG-dimethicones, based on the total weight of the cleansing composition. In some instances, the cleansing composition includes about 0.1 to about 8 wt. %, about 0.1 to about 5 wt. %, about 0.1 to about 3 wt. %, or about 0.1 to about 1 wt. % of the one or more PEG/PPG-dimethicones, based on the total weight of the cleansing composition.

In various embodiments, the cleansing composition is free or essentially free from the one or more silicones other than the PEG/PPG-dimethicones. For instance, the cleansing composition may include less than about 2 wt. %, less than 1 wt. %, less than 0.5 wt. %, less than 0.2 wt. %, less than 0.1 wt. % of the one or more silicones other than the PEG/PPG-dimethicones, based on a total weight of the cosmetic compositions. Further, the cleansing composition may include about 0.001 to about 2 wt. %, about 0.001 to about 1 wt. %, about 0.001 to about 0.5 wt. %, about 0.001 to about 0.1 wt. % of the one or more silicones other than the PEG/PPG-dimethicones, based on the total weight of the cleansing composition.

(h)(ii) Non-Silicone Fatty Compounds

The term "non-silicone fatty compound" means a fatty compound that does not contain any silicon atoms (Si). Non-limiting examples of non-silicone fatty compounds include oils, mineral oil, fatty alcohols, fatty acids, fatty alcohol derivatives, fatty acid derivatives, esters of fatty alcohols, hydroxy-substituted fatty acids, waxes, triglyceride compounds, lanolin, or a combination thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a combination thereof. In some cases, the fatty alcohols are those selected from the group consisting of cetyl alcohol, stearyl alcohol, isostearyl alcohol, oleyl alcohol, and a combination thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a combination thereof. In some cases, the fatty acids are selected from the group consisting of palmitic acid, stearic acid, and a combination thereof.

In some instance, the one or more non-silicone fatty compounds include one or more non-silicone oils. The term "oil" as used herein describes any material which is substantially insoluble in water and substantially liquid at room temperature (25° C.). The oils may be natural oil, synthetic oils, hydrocarbon-based oils, etc., but natural oils are often desired. Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a combination thereof. In some cases, soybean oil may be particularly useful.

The total amount of non-silicone fatty compounds, if present, can vary but are typically in an amount of about 0.001 to about 10 wt. %, based on the total weight of the cleansing composition. In some cases, the total amount of non-silicone fatty compounds is about 0.005 to about 5 wt. %, about 0.005 to about 3 wt. %, about 0.01 to about 10 wt. %, about 0.01 to about 5 wt. %, about 0.01 to about 3 wt. %, or about 0.01 to about 1 wt. % of the one or more non-silicone fatty compounds, based on the total weight of the cleansing composition.

(i) Miscellaneous Ingredients

The cleansing compositions may optionally include one more miscellaneous ingredients. Miscellaneous ingredients are ingredients that are compatible with the cleansing compositions and do not disrupt or materially affect the basic and novel properties of the compositions. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. As an example, hair styling gels, can be found in a variety of different colors (e.g., light blue, light pink, etc.) yet application of the styling gel to hair does not visibly change the color of the hair.

The total amount of the one or more miscellaneous ingredients, if present, will vary. Nonetheless, in various embodiments, the compositions include from about 0.001 to about 10 wt. % of one or more miscellaneous ingredients, based on the total weight of the composition. In further embodiments, the compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the composition.

Viscosity

The viscosity of the cleansing compositions discussed throughout the instant disclosure can vary but are often similar to that of typical cleansing, shampooing, and/or conditioning compositions. Accordingly, in some instances, the viscosity can be from about 2500 cP to about 15,000 cp at a temperature of 25° C. The viscosity measurements can be carried out, for example, at 25° C. measured with a Brookfield DV-LL+Pro Viscometer using Spindle RV 05 and rotational speed of 12% RPM. The test temperature may be maintained at 25° C. by using a Brookfield TC-502P Programmable Refrigerated Bath. From its original container, a sample is transferred into a 600 mL beaker and then tested.

In some cases, the viscosity is from about 2000 cP to about 20,000 cP, about 2000 cP to about 18,000 cP, about 2000 cP to about 15,000 cP, 2000 cP to about 15,000 cP, about 3000 cP to about 20,000 cP, about 3000 cP to about 18,000, about 3000 cP to about 15,000 cP, about 3000 cP to about 12,000 cP, or about 3000 cP to about 10,000 cP. The viscosity can be measured with a Brookfield Viscometer at 25° C.

pH

The pH of the cleansing composition can vary. Nonetheless, in various embodiments, the pH of the cleansing composition is from about 4 to about 8. In certain instances, it is preferable for the pH to be acidic or slightly acidic, having a pH of less than 7. Accordingly, in further embodiments, the pH of the cleansing compositions from about 4 to about 7, about 4 to about 6.5, about 4 to about 6, about 4.5 to about 7, about 4.5 to about 6.5, about 4.5 to about 6, or about 5 to about 6.

PREFERRED EMBODIMENTS

In certain embodiments of the instant disclosure, the cleansing compositions comprises, consists essentially of, or consists of:

(a) about 0.1 to about 5 wt. %, preferably about 0.1 to about 4 wt. %, more preferably about 0.2 to about 3 wt. % of one or more PEG/PPG dimethicones, wherein the one or more PEG/PPG dimethicones are selected from those having from 3 to 30 ethoxy units and from 3 to 30 propoxy units, preferably wherein the one or more PEG/PPG dimethicones are selected from PEG/PPG dimethicones are selected from PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 Dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone, PEG/PPG-27/27, bis-PEG/PPG 18/6 dimethicone, PEG/PPG 30/10 dimethicone, or combinations thereof;

(b) at least 0.5 to about 10 wt. %, preferably about 0.8 to about 8 wt. %, more preferably about 1 to about 5 wt. % of propylene glycol;

(c) about 10 to about 30 wt. %, preferably about 12 to about 25 wt. %, more preferably about 15 to about 20 wt. % of a plurality of surfactants, the plurality of surfactants comprising:

(c)(i) about 5 to about 25 wt. %, preferably about 8 to about 20 wt. %, more preferably about 10 to about 15 wt. % of one or more non-sulfate based anionic surfactants, wherein the one or more non-sulfate anionic surfactants are selected from alkyl sulfonates, acyl amino acid surfactants, acyl isethionates, acyl amino acid surfactants, alkyl sulfosuccinates, alkyl sulfoacetates, alkoxylated monoacids, salts thereof, or combinations thereof;

(c)(ii) about 0.1 to about 15 wt. %, preferably about 1 to about 12 wt. %, more preferably about 1 to about 8 wt. % of one or more amphoteric surfactants, wherein the one or more amphoteric surfactants are selected from betaines, alkyl sultaines, alkyl amphoacetates, alkyl amphoproprionates, salts thereof, or combinations thereof, wherein preferably at least one of the one or more amphoteric surfactants is a betaine, salts thereof, or a combination thereof;

(c)(iii) about 0.1 to about 15 wt. %, preferably about 1 to about 12 wt. %, more preferably about 2 to about 8 wt. % of one or more nonionic surfactants, wherein preferably the one or more nonionic surfactants are selected from esters of polyols with fatty acids (such as glycerol esters), alkanolamides, alkyl polyglucosides, polyoxyalkylenated nonionic surfactants, polyglycerolated nonionic surfactants, ethoxylated fatty esters, or combinations thereof;

preferably, wherein (c)(i) is in a greater amount than (c)(ii), and (c)(iii) is in an amount greater than (c)(ii);

(d) about 0.01 to about 10 wt. %, preferably about 0.1 to about 5 wt. %, more preferably about 0.1 to about 2 wt. % of one or more cationic conditioning polymers, preferably wherein at least one of the one or more cationic conditioning polymers is selected from polyquaterniums, cationic cellulose derivatives, cationic guar derivatives, cationic homopolymers or copolymers derived from acrylic or methacrylic esters or amides, or a combination thereof, or a combination thereof;

(e) optionally, about 0.1 to about 15 wt. %, preferably about 1 to about 10, more preferably about 1 to about 5 wt. % of one or more water-soluble solvents, other than propylene glycol, preferably wherein the one or more water-soluble solvents are selected from glycerin, $C_{2-6}$ mono-alcohols, polyols (polyhydric alcohols), glycols, or combinations thereof;

(f) about 60 to about 85 wt. %, preferably about 65 to about 82 wt. %, more preferably about 70 to about 80 wt. % of water;

(g) optionally, about 0.01 to about 5 wt. %, preferably about 0.1 to about 4, more preferably about 0.1 to about 2 wt. % of one or more thickening agents, wherein preferably the one or more thickening agents are nonionic thickening agents selected from carboxylic acid polymers (including carbomer), crosslinked polyacrylate polymers, polyacrylamide polymers, polysaccharides, gums, or a combination thereof;

(h) about 0.01 to about 5 wt. %, preferably about 0.05 to about 3 wt. %, more preferably less than 1 wt. % of one or more silicones other than the one or more PEG/PPG dimethicones, preferably wherein the one or more silicones, if present, are selected from polyorganosiloxanes, polyalkylsiloxanes, polyarylsiloxanes, polyalkarylsiloxanes, polyestersiloxanes, and a combination thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a combination thereof, and (i) optionally, about 0.1 to about 10 wt. %, preferably about 1 to about 8 wt. %, more preferably about 1 to about 5 wt. % of one or more miscellaneous ingredients;

wherein all weight percentages are based on the total weight of the composition; and wherein the composition is free from sulfate-based surfactants.

Further to the above, the plurality of surfactants, in a preferred embodiment, comprise, consist essentially of, or consist of:

(c)(i) about 5 to about 25 wt. %, preferably about 8 to about 20 wt. %, more preferably about 10 to about 15 wt. % of one or more non-sulfate based anionic surfactants, wherein at least one of the one or more non-sulfate anionic surfactants is an alkyl sulfonate selected from $C_8$-$C_{16}$ alkyl benzene sulfonates, $C_{10}$-$C_{20}$ paraffin sulfonates, $C_{10}$-$C_{24}$ olefin sulfonates, salts thereof, or combinations thereof, preferably wherein the at least one alkyl sulfonate is a $C_{10}$-$C_{24}$ olefin sulfonates, more preferably $C_{14}$-$C_{16}$ olefin sulfonate; and/or at least one of the one or more non-sulfate anionic surfactants is an acyl sarcosinate, preferably wherein the at least one acyl sarcosinate is selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, salts thereof, or combinations thereof, preferably sodium lauryl sarcosinate;

(c)(ii) about 0.1 to about 15 wt. %, preferably about 1 to about 10 wt. %, more preferably about 1 to about 5 wt. % of one or more amphoteric surfactants, wherein at least one of the one or more amphoteric surfactants is a betaine selected from cocamidopropyl betaine, coco betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, salts thereof, or combinations thereof; and (c)(iii) about 0.1 to about 15 wt. %, preferably about 1 to about 12 wt. %, more preferably about 2 to about 8 wt. % of one or more nonionic surfactants, wherein preferably the one or more nonionic surfactants are selected from esters of polyols with fatty acids (such as glycerol esters), alkanolamides, alkyl polyglucosides, polyoxyalkylenated nonionic surfactants, polyglycerolated nonionic surfactants, ethoxylated fatty esters, or combinations thereof.

In even further embodiments, the plurality of surfactants preferably comprises, consists essentially of, or consists of:

(c)(i) about 5 to about 25 wt. %, preferably about 8 to about 20 wt. %, more preferably about 10 to about 15 wt. % of one or more non-sulfate based anionic surfactants comprises, consists essentially of, or consists of;

about 1 to about 20 wt. %, preferably about 2 to about 15 wt. %, more preferably about 5 to about 15 wt. % of one or more alkyl sulfonates selected from $C_8$-$C_{16}$ alkyl benzene sulfonates, $C_{10}$-$C_{20}$ paraffin sulfonates, $C_{10}$-$C_{24}$ olefin sulfonates, salts thereof, or combinations thereof, preferably wherein the at least one alkyl sulfonate is a $C_{10}$-$C_{24}$ olefin sulfonates, more preferably $C_{14}$-$C_{16}$ olefin sulfonate; and about 0.1 to about 15 wt. %, preferably about 1 to about 12 wt. %, more preferably about 1 to about 5 wt. % of one or more acyl sarcosinates selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, salts thereof, or combinations thereof, preferably sodium lauryl sarcosinate;

(c)(ii) about 0.1 to about 15 wt. %, preferably about 1 to about 12 wt. %, more preferably about 1 to about 8 wt. % of one or more amphoteric surfactants, wherein at least one of the one or more amphoteric surfactants is a betaine selected from cocamidopropyl betaine, coco betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, salts thereof, or combinations thereof; and (c)(iii) about 0.1 to about 15 wt. %, preferably about 1 to about 12 wt. %, more preferably about 2 to about 8 wt. % of one or more nonionic surfactants, wherein preferably the one or more nonionic surfactants are selected from esters of polyols with fatty acids (such as glycerol esters), alkanolamides, alkyl polyglucosides, polyoxyalkylenated nonionic surfactants, polyglycerolated nonionic surfactants, ethoxylated fatty esters, or combinations thereof wherein (c)(i) is in a greater amount than (c)(ii); (c)(iii) is in an amount greater than (c)(ii); and (c)(i) is in a greater amount than (c)(iii);

In further embodiments, the cleansing compositions preferably comprises, consists essentially of, or consists of:

(a) about 0.1 to about 5 wt. %, preferably about 0.1 to about 4 wt. %, more preferably about 0.2 to about 3 wt. % of one or more PEG/PPG dimethicones selected from PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 Dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone, PEG/PPG-27/27, bis-PEG/PPG 18/6 dimethicone, PEG/PPG 30/10 dimethicone, or combinations thereof;

(b) at least 0.5 to about 10 wt. %, preferably about 0.8 to about 8 wt. %, more preferably about 1 to about 5 wt. % of propylene glycol;

wherein (a) and (b) are in a weight ratio of 1:2 to 1:20 ((a):(b)), preferably about 1:2 to about 1:15, more preferably about 1:2 to about 1:10;

(c) about 10 to about 30 wt. %, preferably about 12 to about 25 wt. %, more preferably about 15 to about 20 wt. % of a plurality of surfactants, the plurality of surfactants comprising:

(c)(i) about 5 to about 25 wt. %, preferably about 8 to about 20 wt. %, more preferably about 10 to about 15 wt. % of one or more non-sulfate based anionic surfactants that comprises, consists essentially of, or consists of;

about 1 to about 20 wt. %, preferably about 2 to about 15 wt. %, more preferably about 5 to about 15 wt. % of one or more alkyl sulfonates selected from $C_8$-$C_{16}$ alkyl benzene sulfonates, $C_{10}$-$C_{20}$ paraffin sulfonates, $C_{10}$-$C_{24}$ olefin sulfonates, salts thereof, or combinations thereof, preferably wherein the at least one alkyl sulfonate is a $C_{10}$-$C_{24}$ olefin sulfonates, more preferably $C_{14}$-$C_{16}$ olefin sulfonate; and about 0.1 to about 15 wt. %, preferably about 1 to about 12 wt. %, more preferably about 1 to about 5 wt. % of one or more acyl sarcosinates, preferably wherein the one or more acyl sarcosinates are selected from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, salts thereof, or combinations thereof, preferably sodium lauryl sarcosinate;

(c)(ii) about 0.1 to about 15 wt. %, preferably about 1 to about 12 wt. %, more preferably about 1 to about 8 wt. % one or more amphoteric surfactants, wherein at least one of the one or more amphoteric surfactants is a betaine selected from cocamidopropyl betaine, coco betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, salts thereof, or combinations thereof; and (c)(iii) about 0.1 to about 15 wt. %, preferably about 1 to about 12 wt. %, more preferably about 2 to about 8 wt. % of one or more nonionic surfactants, wherein preferably the one or more nonionic surfactants are selected from esters of polyols with fatty acids (such as glycerol esters), alkanolamides, alkyl polyglucosides, polyoxyalkylenated nonionic surfactants, polyglycerolated nonionic surfactants, ethoxylated fatty esters, or combinations thereof wherein (c)(i) is in a greater amount than (c)(ii); (c)(iii) is in an amount greater than (c)(ii); and (c)(i) is in a greater amount than (c)(iii);

(d) about 0.01 to about 10 wt. %, preferably about 0.1 to about 5 wt. %, more preferably about 0.1 to about 3 wt. % of one or more cationic conditioning polymers, preferably wherein at least one of the one or more cationic conditioning polymers is selected from polyquaterniums, cationic cellulose derivatives, cationic guar derivatives, cationic homopolymers or copolymers derived from acrylic or methacrylic esters or amides, or a combination thereof, or a combination thereof;

(e) optionally, about 0.1 to about 15 wt. %, preferably about 1 to about 10, more preferably about 1 to about 5 wt. % of one or more water-soluble solvents, other than propylene glycol, preferably wherein the one or more water-soluble solvents are selected from glycerin, $C_{2-6}$ mono-alcohols, polyols (polyhydric alcohols), glycols, or combinations thereof;

(f) about 60 to about 85 wt. %, preferably about 65 to about 82 wt. %, more preferably about 70 to about 80 wt. % of water;

(g) optionally, about 0.01 to about 5 wt. %, preferably about 0.1 to about 4 wt. %, more preferably about 0.1 to about 3 wt. % of one or more thickening agents, wherein preferably the one or more thickening agents are nonionic thickening agents selected from carboxylic acid polymers (including carbomer), crosslinked polyacrylate polymers, polyacrylamide polymers, polysaccharides, gums, or a combination thereof;

(h)(i) about 0.01 to about 5 wt. %, preferably about 0.05 to about 3 wt. %, more preferably, less than 0.3 wt. % of one or more silicones other than the one or more PEG/PPG dimethicones, preferably wherein the one or more silicones, if present, are selected from polyorganosiloxanes, polyalkylsiloxanes, polyarylsiloxanes, polyalkarylsiloxanes, polyestersiloxanes, and a combination thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a combination thereof, (h)(ii) optionally, about 0.001 to about 10 wt. %, preferably about 0.005 to about 5 wt. %, more preferably about 0.01 to about 2 wt. % of one or more non-silicone fatty compounds, preferably wherein the one or more non-silicone fatty compounds, if present, are selected from oils, mineral oil, fatty alcohols, fatty acids, fatty alcohol derivatives, fatty acid derivatives, esters of fatty alcohols, hydroxy-substituted fatty acids, waxes, triglyceride compounds, lanolin, or a combination thereof, preferably vegetal oils; and (i) optionally, about 0.1 to about 10 wt. %, preferably about 0.1 to about 8 wt. %, more preferably about 1 to about 5 wt. % of one or more miscellaneous ingredients, preferably wherein the one or more miscellaneous ingredients are selected from preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants;

wherein all weight percentages are based on the total weight of the composition; and wherein the composition is free from sulfate-based surfactants.

The cleansing composition described throughout the disclosure, as mentioned previously, are surprising effective for preserving the color of artificially colored hair. Thus, in various embodiments, the cleansing composition preserves color of the artificially colored hair compared to a comparative cleansing composition lacking the PEG/PPG dimethicone but otherwise identical to the cleansing composition and preserves color of the artificially colored hair compared to a comparative cleansing composition lacking the propylene glycol but otherwise identical to the cleansing composition.

Methods

The cleansing compositions of the instant disclosure are particularly useful for cleansing and conditioning hair or skin. Additionally, the cleansing compositions are useful for preserving color in artificially colored hair. The cleansing compositions provide a variety of desirable cosmetic and styling benefits to the hair, for example, smoothness, detangling, and shine. Accordingly, the cleansing compositions are useful in methods for cleansing hair and skin, methods of conditioning hair and skin, and methods for imparting smoothness, detangling, and/or shine to hair. In addition, the cleansing compositions are useful in methods of preserving color of artificially colored hair. The methods typically comprise application of the cleansing composition to the hair (or skin). The cleansing compositions can be massed or spread throughout the hair (or skin) and subsequently rinsed from the hair (or skin).

In some cases, the methods include shampooing and/or conditioning the hair with a cleansing composition of the instant disclosure. Such methods typically include applying an effective amount of a cleansing composition to the hair, massaging or spreading the composition throughout the hair, and subsequently rinsing the cleansing composition from the hair. Usually, the cleansing composition is merely allowed to remain on the hair for a period sufficient to incorporate the cleansing composition throughout the hair, for example, by lathering the composition throughout the hair using one's hands. As is common when using shampoo and/or conditioning compositions, the hair may be wetted or rinsed with water prior to application of a cleansing composition. Having water already in the hair can be helpful for creating lather when applying the cleansing compositions because the water interacts with the surfactants of the surfactant system.

EXAMPLES

Various changes can be made in the above-described compositions and methods without departing from the scope of the invention. Accordingly, it is intended that all disclosure contained in the above description and in the examples given below, shall be interpreted as illustrative and not in a limiting sense.

EXAMPLE 1

| | | | A | B | C |
|---|---|---|---|---|---|
| (a) | PEG/PPG - Dimethicone | PEG-PPG-4/12 Dimethicone | 0.25 | | 0.25 |
| (b) | Propylene Glycol | Propylene Glycol | 1.24 | 1.24 | 0.4[1] |
| | Ratio of (a):(b) | | 1:5 | NA | 1:1.6 |
| (c)(i) | Anionic surfactants | Sodium C14-16 Olefin Sulfonate | 10 | 10 | 10 |
| | | Sodium Lauryl Sarcosinate | 1.5 | 1.5 | 1.5 |
| | Total Anionic Surfactants | | 11.5 | 11.5 | 11.5 |
| (c)(ii) | Amphoteric Surfactants | Cocamidopropyl Betaine | 2 | 2 | 2 |
| | | Coco Betaine | 0.4 | 0.4 | 0.4 |
| | Total Amphoteric Surfactants | | 2.4 | 2.4 | 2.4 |
| (c)(ii) | Nonionic Surfactants | Glycol Distearate, PEG-150 Distearate, Cocamide MIPA, PEG-55-Propylene Glycol Oleate, and/or Trideceth-6 | 4.7 | 4.7 | 4.7 |
| | Total Nonionic Surfactants | | 4.7 | 4.7 | 4.7 |
| | Total Surfactants | | 18.6 | 18.6 | 18.6 |
| (d) | Cationic Polymer | Polyquaternium-7 and/or Hydroxypropyl Guar Hydroxypropyltrimonium Chloride | 0.4 | 0.4 | 0.4 |
| (e) | Water-Soluble Solvent | Glycerin and/or Hexylene Glycol | 3 | 3 | 3 |
| (g) | Thickener | Carbomer | 0.2 | 0.2 | 0.2 |
| (h)(i) | Silicone Oil | Amodimethicone | 0.1 | 0.1 | 0.1 |

-continued

| EXAMPLE 1 | | | | | |
|---|---|---|---|---|---|
| | | | A | B | C |
| (h)(ii) | Non-Silicone Oil | *Glycine Soja* (Soybean) oil | 0.01 | 0.01 | 0.01 |
| (i) | Miscellaneous[1] | Preservatives, Amino Acids, pH adjustors, cationic surfactant | ≤5 | ≤5 | ≤5 |
| (f) | Water | | QS | QS | QS |
| | pH | | 5.4 | 5.3 | 5.3 |
| | Viscosity[2] | | 5400 | 6000 | 8300 |

[1]This amount of propylene glycol comes from the addition of the ingredient "propylene glycol (and) PEG-55 propylene glycol oleate," which is a mixture of propylene glycol and PEG-55 propylene glycol oleate. The ingredient is included as a source of PEG-55 propylene glycol oleate, not or its propylene glycol content. The propylene glycol is an ancillary component, perhaps used to solubilize or stabilize the PEG-55 propylene glycol oleate.

[1]Sodium benzoate, tocopherol, salicylic acid, arginine, serine, glutamic acid, citric acid, sodium hydroxide, cetrimonium chloride

[2]at 25 C. measured with a Brookfield DV-LL+ Pro Viscometer using Spindle RV 05 and rotational speed of 12% RPM.

Example 2

Testing was carried out with the cleansing compositions of Example 1 to investigate the roles of the PEG/PPG dimethicone and the propylene glycol. Commercially available 90% grey hair swatches (SA20, 2.7 g, 27 cm) were obtained and initially cleansed with a standard shampoo. After cleansing the hair swatches, the hair swatches were dyed with a standard commercially available oxidative dye (6Rr, light and intense red color). Subsequently, the cleansing compositions of Example 1 were individually used to shampoo the artificially colored hair swatches. The compositions of Example 1 were applied to the artificially colored hair swatches (about 1 gram composition per 1 gram hair) and massaged into the hair before and then rinsed from the hair. The water used for rinsing the various hair swatches was collected and visually compared by three individuals to determine the amount of color removed from the hair during rinsing (to measure color loss). After the compositions of Example 1 were rinsed from the hair, the hair swatches were blow dried. The cycle of washing the hair, rinsing the hair, and drying the hair was repeated until the hair swatches had been cleansed with the compositions of Example 1 six times. After completion of the six cycles, three lab experts independently evaluated the hair swatches and rinse water to determine color loss, shine, smoothness, moisturization, and tactile feel. Using Composition "A" as the benchmark, the lab experts evaluated the hair swatches using the following scale:

"1" Better than benchmark;

"2" Somewhat better than benchmark;

"3" Equivalent to benchmark;

"4" Somewhat inferior to benchmark; and

"5" Inferior to benchmark.

This procedure shows how cleansing artificially colored hair with Inventive Composition A compares to cleansing hair with Comparative Compositions B and C. The only differences between Inventive Composition A and Comparative Compositions B and C are the lack of PEG/PPG dimethicone in Composition B and the lack of propylene glycol in Composition C. The testing provides a side-by-side comparison highlighting the individual impact of a PEG/PPG dimethicone and the individual impact of propylene glycol. The scores from the three lab experts were averaged and presented Below.

| | A | B | C |
|---|---|---|---|
| Color Loss in Rinsing | Benchmark | 4 | 4 |
| Shine | | 2 | 4 |
| Smoothness of Dry Hair | | 4 | 5 |
| Moisturized Feel of Dry Hair | | 4 | 4 |
| Tactile Feel of Dry Hair | | 5 | 5 |

The data show that cleansing artificially colored hair with Inventive Composition A resulted in less color loss (improvements in color retention) than cleansing the artificially colored hair with Comparative Compositions B and C. The benefits provided by Inventive Composition A, however, were not limited to color retention. In addition, cleansing with Inventive Composition A resulted in the hair being more smooth, more moisturized, and having a better tactile feel compared to hair cleansed with the Comparative Compositions B and C. These results (improved color retention, smoothness, moisturization, and overall tactile feel) were not predictable. The extent of improvements and the fact that Composition A provided improvements with respect to a multitude of cosmetically desirable properties is surprising. It is also surprising to find the relatively small amounts of PEG/PPG dimethicone and propylene glycol used in Composition A provided such dramatic improvements. Composition C includes a small amount of propylene glycol and includes hexylene glycol. The comparison of Composition A and C, however, illustrates the relatively small increase in the amount of propylene glycol improved color retention, smoothness, moisturization, and overall tactile feel of the hair.

The foregoing disclosure illustrates and describes embodiments of the invention. The disclosure shows and describes only the preferred embodiments, but it is understood that the invention is useable in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" is the same as "mixtures thereof" and is interchangeable with "a combination thereof" and "combinations thereof." Throughout the disclosure, the term "a combination thereof" may be used following a list of elements as shown in the following example where letters A-F represent the elements: "one or more elements selected from the group consisting of A, B, C, D, E, F, and a combination thereof." The term, "a combination thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of ingredients identified for the cleansing compositions may overlap. In such cases where overlap may exist and the composition/product includes two overlapping ingredients (or more than two overlapping ingredients), an overlapping ingredient does not represent more than one component. For example, a fatty acid may be defined as both a "fatty compound" and separately as a "surfactant." If a particular claimed composition/product includes both a fatty compound and a surfactant, a single fatty acid in a composition can serve as only the fatty compound or as only the emulsifier (a single fatty is not considered to simultaneously qualify as both the fatty compound and the surfactant).

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants, to the extent they exist, even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded. In other words, the cleansing compositions of the instant disclosure may be free or essentially free of any one or more of the components positively set forth in the instant disclosure.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention). Similarly, when a composition is essentially free from a particular element, the composition may include less than 1 wt. %, less than 0.5 wt. %, less than 0.1 wt. %, less than 0.05 wt. %, or less than 0.01 wt. %, or none of the specified material. Furthermore, all components that are positively set forth in the instant disclosure may be essentially excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition free from sulfate-based surfactants, comprising:
- (a) about 0.1 to about 5 wt. % of one or more PEG/PPG dimethicones;
- (b) at least 0.5 to about 10 wt. % of propylene glycol:
- (c) about 10 to about 30 wt. % of a plurality of surfactants, the plurality of surfactants comprising:
  - (c)(i) a mixture of one or more alkyl sulfonate anionic surfactant or salt thereof and one or more acyl sarcosinate anionic surfactant or salt thereof;
  - (c)(ii) one or more amphoteric surfactants; and
  - (c)(iii) one or more nonionic surfactants;
- (d) one or more cationic conditioning polymers;
- (e) optionally, about 0.1 to about 15 wt. % of one or more water-soluble organic solvents other than propylene glycol; and (f) about 60 to about 85 wt. % of water; wherein all weight percentages are based on the total weight of the composition; and wherein the composition is free from sulfate-based surfactants.

2. The composition of claim 1, wherein the one or more PEG/PPG dimethicones are selected from those having from 3 to 30 ethoxy units and from 3 to 30 propoxy units.

3. The composition of claim 1, wherein the one or more PEG/PPG dimethicones are selected from the group consisting of PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 Dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone, PEG/PPG-27/27, bis-PEG/PPG 18/6 dimethicone, and PEG/PPG 30/10 dimethicone.

4. The composition of claim 1, wherein (a) and (b) are in a weight ratio of 1:1 to 1:20; and/or (c)(i) is in an amount greater than (c)(ii), (c)(iii) is in an amount greater (c)(ii), and (c)(i) is in an amount greater than (c)(iii).

5. The composition of claim 1, wherein the at least one alkyl sulfonate is selected from the group consisting of $C_8$-$C_{16}$ alkyl benzene sulfonates, $C_{10}$-$C_{20}$ paraffin sulfonates, $C_{10}$-$C_{24}$ olefin sulfonates, and salts thereof.

6. The composition of claim 5 wherein the at least one alkyl sulfonate is a $C_{10}$-$C_{24}$ olefin sulfonate or a salt thereof.

7. The composition of claim 1 wherein the at least one acyl sarcosinate is selected from the group consisting of potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

8. The composition of claim 1, wherein the one or more amphoteric surfactants are selected from the group consisting of betaines, alkyl sultaines, alkyl amphoacetates, alkyl amphoproprionates, and salts thereof.

9. The composition of claim 8 wherein at least one of the one or more amphoteric surfactants is selected from betaines and salts thereof.

10. The composition of claim 1, wherein the one or more nonionic surfactants are selected from the group consisting of fatty acid esters of polyols, fatty acid alkanolamides, alkyl polyglucosides, polyoxyalkylenated nonionic surfactants, polyglycerolated nonionic surfactants, and ethoxylated fatty esters.

11. The composition of claim 1, wherein the one or more cationic conditioning polymers are selected from the group consisting of polyquaterniums, cationic cellulose derivatives, cationic guar derivatives, and cationic homopolymers or copolymers derived from acrylic or methacrylic esters or amides.

12. The composition of claim 1 comprising one or more water-soluble organic solvents other than propylene glycol selected from the group consisting of glycerin, $C_{2-6}$ mono-alcohols, polyols, and glycols.

13. A cleansing composition free from sulfate-based surfactants, comprising:

(a) about 0.1 to about 2 wt. % of one or more PEG/PPG dimethicones;

(b) about 0.5 to about 10% of propylene glycol:

(c) about 15 to about 25 wt. % of a plurality of surfactants, the plurality of surfactants comprising:

(c)(i) about 5 to about 15 wt. % of a mixture of one or more alkyl sulfonate anionic surfactants or salts thereof and one or more acyl sarcosinate anionic surfactants or salts thereof;

(c)(ii) about 1 to about 8 wt. % of one or more amphoteric surfactants; and (c)(iii) about 2 to about 10 wt. % of one or more nonionic surfactants; wherein (c)(i) is in an amount greater than (c)(ii), (c)(iii) is in an amount greater (c)(ii), and (c)(i) is in an amount greater than (c)(iii);

(d) one or more cationic conditioning polymers;

(e) about 0.1 to about 15 wt. % of one or more water-soluble organic solvents other than propylene glycol;

(f) about 70 to about 85 wt. % of water;

(g) optionally, about 0.1 to about 5 wt. % of one or more thickening agents;

(h) less than 0.3 wt. % of one or more silicones other than the one or more PEG/PPG dimethicones; and (i) optionally, about 0.1 to about 10 wt. % of one or more miscellaneous ingredients; wherein all weight percentages are based on the total weight of the composition; and wherein the composition is essentially free from sulfate-based surfactants.

14. A method for cleansing hair comprising:

(a) applying the cleansing composition of claim 1 to the hair; and (b) rinsing the cleansing composition from the hair.

15. The method of claim 14, wherein the hair is artificially colored hair.

16. The method of claim 14, wherein cleansing the hair with the cleansing composition preserves the color of the artificially colored hair compared to cleansing the hair with a first comparative cleansing composition lacking the PEG/PPG dimethicone but otherwise identical to the cleansing composition and compared to cleansing the hair with a second comparative cleansing composition lacking the propylene glycol but otherwise identical to the cleansing composition.

17. A method for cleansing and preserving color of artificially colored hair comprising:

(a) applying the cleansing composition of claim 1 to artificially colored hair; and (b) rinsing the cleansing composition from the artificially colored hair;

wherein cleansing the hair with the cleansing composition preserves color of the artificially colored hair compared to cleansing the hair with a first comparative cleansing composition lacking the PEG/PPG dimethicone but otherwise identical to the cleansing composition and compared to cleansing the hair with a second comparative cleansing composition lacking the propylene glycol but otherwise identical to the cleansing composition.

* * * * *